United States Patent [19]

Bowen

[11] 4,178,499

[45] Dec. 11, 1979

[54] HEATING UNIT INDICATOR FOR DISINFECTING SOFT LENSES, OR THE LIKE

[75] Inventor: John G. Bowen, Santa Ana, Calif.

[73] Assignee: Rincon Industries, Inc., Woodland Hills, Calif.

[21] Appl. No.: 835,420

[22] Filed: Sep. 21, 1977

[51] Int. Cl.² ........................................... F27D 11/02
[52] U.S. Cl. .................................. 219/439; 422/307; 115/114 V; 116/114 Y; 116/217; 219/328; 219/385; 219/430; 219/442; 219/521
[58] Field of Search ............... 219/214, 385, 386, 387, 219/327, 328, 430, 437, 438, 439, 441, 442, 513, 521, 530; 116/114 Y, 114 V, 114.5; 21/89, 92, 119, 120

[56] References Cited

U.S. PATENT DOCUMENTS

| | | | |
|---|---|---|---|
| 3,067,015 | 12/1962 | Lawdermilt | 116/114 V |
| 3,130,288 | 4/1964 | Monaco et al. | 291/385 |
| 3,294,039 | 12/1966 | Ogden | 219/439 X |
| 3,764,780 | 10/1973 | Ellis | 219/430 |
| 3,851,861 | 12/1974 | Cummins et al. | 219/328 X |
| 3,961,893 | 6/1976 | Russell et al. | 219/92 X |
| 3,998,590 | 12/1976 | Glorieux | 219/439 X |

*Primary Examiner*—Volodymyr Y. Mayewsky
*Attorney, Agent, or Firm*—Keith D. Beecher; Jessiup & Beecher

[57] ABSTRACT

An indicator is provided for a heating unit which may be used as a soft contact lens disinfecting unit and which embodies an exterior construction entirely of thermoplastic material. Wax contained in the unit is used as a heat transfer medium, as a temperature stabilization means, as a heat sotrage medium, and, in accordance with the present invention, as a unique indicator system which enables the user to confirm when the unit has reached the proper operating temperature. The heating unit to be described, is specifically constructed to produce or aid in disinfecting so-called soft contact lenses intended for wearing in contact with the eye. The unit is more generally applicable, and may be used to advantage, when a low cost heating unit is desired which will raise the temperature of an object or a material to a given temperature, maintain it at or above the given temperature for a given time period, and then allow it to cool down and return to an ambient temperature condition.

3 Claims, 3 Drawing Figures

HEATING UNIT INDICATOR FOR DISINFECTING SOFT LENSES, OR THE LIKE

RELATING COPENDING APPLICATIONS

Ser. No. 834,104 Lamont J. Seitz, Filed: Sept. 19, 1977.

BACKGROUND OF THE INVENTION

It is necessary to produce periodically an essentially disinfected condition in soft contact lenses so that bacterial organisms or their by-products will not cause harm to the wearer's eyes. Since the soft lens material is permeable to liquids, soaking the lens in strong germicidal solutions will result in the lens becoming impregnated with the solution, and this can lead to irritation to the user's eye when the lens is worn. In general, it has been found difficult, if not impossible, to disinfect soft lens by treatment with chemical or biochemical solutions which will not cause eye irritation to at least some percentage of the wearers.

As an alternate means for producing the desired disinfected condition in the soft lens, heat may be used. The lens must be kept immersed in physiologically normal saline solution, or its equivalent, when it is not being worn, to prevent the lens material from drying out. Heat is therefore generally applied by first placing the lens in a suitable container or lens holder; adding a suitable amount of saline solution, of the proper concentration, so that the lens is totally immersed; closing or covering the lens container; placing the lens container in a suitable heating unit; and energizing the heating unit.

The heating unit must raise the temperature of the saline solution and immersed lens to the required temperature, hold the lens at or above this termperature for the required time, and then allow it to cool to ambient temperature. Typical values of the time and temperature deemed suitable for producing the disinfected condition require the lens to be maintained at or above 80° C., for a period of 10 minutes or more. Since aging of the lens material is accelerated by excessive temperatures and/or by extended time at elevated temperatures, it is desirable that the heating unit be controlled so that excessive temperatures, or excessive time at elevated temperatures, will not shorten the life of the lens.

It is also highly desirable that the lens user be able to check periodically on the proper operation of the heating unit to insure that the unit has reached the desired temperature. An indicator light on a typical prior art heating unit only tells the user that the unit is connected to a functioning electrical source, and that the unit has been turned on. The light may well function normally even if the heating element in the prior art unit is defective and the lens has not reached the proper temperature.

The heating unit must be designed with careful attention to electrical safety/shock hazard considerations since the user typically uses the unit in a bathroom adjacent to grounded water piping and wash basins. Since the typical household electrical outlets are only two contact, without grounding pin provisions, it is impractical to use a 3-wire power cord with a ground connection to any exposed metallic portions of the device. The user of the prior art unit is therefore potentially subject to a significant shock hazard if he touches a grounded object such as a water faucet while in contact with any metallic portion of the heating unit. Any current leakage path between the electrical circuitry and the exposed metallic portion of the prior art unit can lead to potentially fatal shock hazards under these conditions. It would therefore be very advantageous to have the heating unit constructed so that there is no exposed or exposable portion of the unit constructed of metal or other electrically conductive materials. The Co-pending application Ser. No. 834,104 discloses such a heating unit.

An objective of the present invention is to provide in a heating unit of the type disclosed in the copending application, a simple and inexpensive means for the user to observe when the proper temperature has been reached during the operation of the unit, and a postive end-of-heating-cycle indication, readily visible to the user.

DETAILED DESCRIPTION OF THE ILLUSTRATED EMBODIMENT

Figure 1:
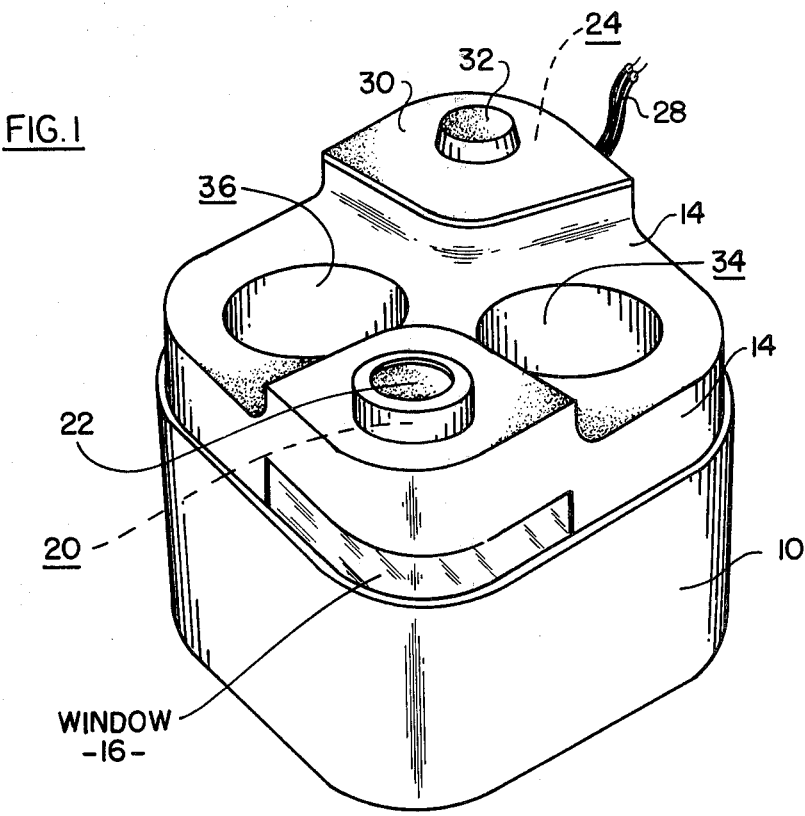
FIG. 1 is a perspective representation of a heating unit, with its cover removed, and including an indicator constructed in accordance with one embodiment of the invention.
Figure 2:
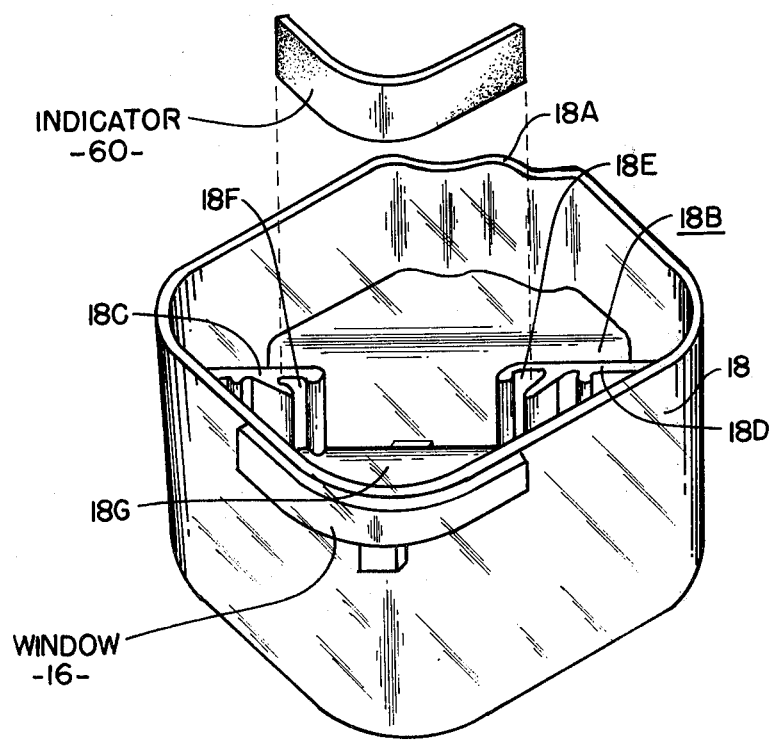
FIG. 2 is a perspective view of a bowl portion of the unit of FIG. 1.

The heater unit shown in FIG. 1, for example, includes a housing 10, and a bowl 18 (FIG. 2), which fits into the housing. A transparent strip forming a window 16 is mounted on the bowl 18, and at least the portion of the bowl behind the strip is transparent so that an indicator 60 may be observed through the window when the unit has reached its operating temperature. An incubator 14 (FIGS. 1 and 3) is supported in the bowl 18, shown in FIG. 1. The housing 10 serves to insulate the user against the high temperatures within the unit. The housing may be molded from a high operating temperature grade of opaque thermoplastic, such as polycarbonate.

An air space is provided between the inner wall of housing 10 and the outer wall of bowl 18. This air space acts as an insulating means and prevents the outer surface of housing 10 from reaching uncomfortable temperatures. The housing 10 is joined to bowl 18 preferably by ultrasonic welding to form a joint between the bottom edge of bowl 18 and the inside bottom surface of housing 10. A cover is provided (not shown) which serves to reduces heat loss in the unit during the disinfection cycle, and which also serves to prevent dust and dirt from settling on the internal components of the unit.

The incubator 14 may be molded from an opaque high operating temperature grade of plastic such as polycarbonate. The incubator contains two wells 34 and 36 of suitable dimensions to accept the maximum vial size to be used as lens holders during the heating/disinfecting operation of the unit. The top of the molded form constituting incubator 14 also contains a switch cavity 24 and a wax fill hole 20.

Bowl 18 may be molded from a high operating temperature transparent plastic, such as polycarbonate, as may the window 16. Two indicator mounting walls 18C and 18D extend vertically and terminate in indicator mounting notches 18E and 18F. A recess 18B extends to the bowl bottom. The top edge 18A extends around the top periphery of bowl 18 in a continuous plane which ultimately mates with and is welded to incubator 14.

The indicator 60 may be molded or formed from high operating temperature plastic such as polycarbonate, and it is fitted into notches 18E and 18F. The color of the indicator is selected to be highly visible to the eye, and preferably is made to be some shade of red. Indicator 60 may be secured in the indicator mounting notches 18E and 18F of bowl 18 by the application of an appropriate plastic adhesive.

The bottom edge of indicator 60 fits closely against the surface of step 18G. In conjuction with the indicator mounting walls 18C and 18D, the indicator forms a liquid-tight dam across step 18G. Liquid in the area between window 16 and indicator 60 is retained by the dam.

During operation of the unit, as will be described, bowl 18 is filled with liquid wax. The dam formed by indicator 60 and indicator mounting walls 18C and 18D traps and retains the liquid wax when the unit is hot and the wax is molten. As the wax solidifies, its volume decreases substantially. If it were not for the damming effect of indicator 60, the level of the solid wax in the unit could fall below the top of window 16, and thus allow part of indicator 60 to be visible when the unit is cold. The small amount of shrinkage in the wax trapped by the dam, prevents this from occurring.

A thermostatic switch is mounted in switch cavity 24. In order to provide a cover over the thermostatic switch and the electrical connections in switch cavity 24, a switch cover 30 is provided. The switch cover 30 may be injection molded from an opaque grade of high operating temperature plastic such as polycarbonate. The cover contains a hole in its top surface, and a resilient boot 32, which may be molded from a suitable high operating temperature elastomer such as krayton, is mounted in the hole. Boot 32 provides a flexible cover for the operating push-botton of the switch, and allows operation of the push-button while sealing the switch cavity 24 against dust and moisture.

Figure 3:
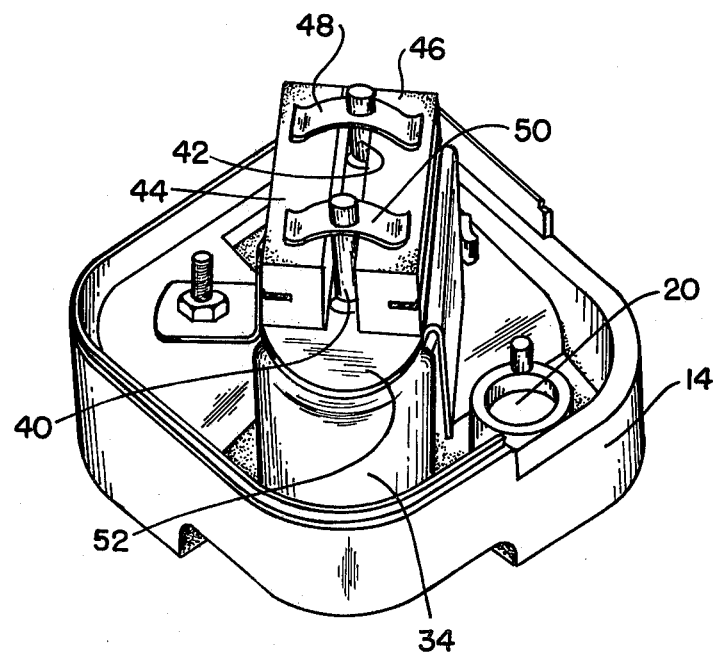
FIG. 3 is an inverted perspective view of an incubator portion of the assembly of FIG. 1, which fits into the bowl portion.

Electrical heating means is maintained within housing 10. The electrical heating means may be any appropriate type of electrically energized heater. For example, as shown in FIG. 3, two resistors 44 and 46 may be used as low cost heating elements. These resistors may be mounted on the underside of wells 34 and 36 by posts 40 and 42, and push-on speed nuts 48 and 50. The resistors may have ceramic casings, and may be of the type designated PW22, manufactured by the International Resistance Corporation, a subsidiary of the TRW Company. A heat conducting member 52 may be mounted between the resistors and the undersides of wells 34 and 36. Details of the structure shown in FIG. 3 are described in copending application 834,104. The heating means is energized through a cable 28 and controlled by the switch in the cavity 24. After the mechanical and electrical assembly of incubator 14 has been completed, the incubator 14 is joined and sealed to the bowl 18 to form the assembly shown in FIG. 1. The joining operation, preferably ultrasonic welding, forms an essentially hermetic seal between the two components. The top edge 18A of bowl 18 is welded to a flange area 58 of incubator 14 to form the seal. The window 16 provides a means through which indicator 60 can be observed when the proper operating temperature has been reached, as will be described.

After the incubator and bowl have been sealed together, the unitis filled with molten wax through the wax fill hole 20 at a temperature of approximately 100° C., to the level of the base of the wax fill hole 20. A plug 22 is not seated into the wax fill hole 20, and is sealed in place, preferably by ultrasonic welding, so as to provide a leak-tight containment for the wax. The wax preferably is a typical hydrocarbon paraffin wax available from major oil refineries. The wax may have its characteristics modified slightly by the addition of clear mineral oil up to 20% by volume. The addition of mineral oil results in a whiter, more opaque appearing wax, when in its solid state.

The wax within the heating unit of the invention performs a number of functions. For example, when the unit is cold, at the start of a disinfection cycle, the wax is in a solid state. The solid wax is a white opaque material which is visible through window 16. The opaque wax completely blocks the view through window 16 of indicator 60 of FIG. 2.

When the heating unit of the invention approaches its operating temperature in the disinfection cycle, the wax between window 16 and indicator 60 melts and becomes a water clear liquid. Indicator 60 is now readily visible through window 16 and through the molten wax. The combination of the wax, window 16 and indicator 60 provides, therefore, a positive indicator to the user when the proper disinfection temperatures have been reached.

As the unit cools down, after the disinfection cycle, the wax gradually returns to the solid white opaque state, and indicator 60 is no longer visible through window 16. When the indicator 60 is no longer visible, and the window 16 has returned to the view of the white wax, the user has a positive indication that the disinfection cycle has beem completed, and that the lenses have been properly disinfected.

The wax within the unit also acts as a heat transfer medium. When the unit is cold, and when it is energized by depressing the manually activated thermostatic switch in cavity 24, the heating element within the housing begins to heat up. This action causes the solid wax adjacent the heating element to melt, and the melted liquid wax then begins to circulate by convection. The hot wax tends to rise, carrying heat to the unmelted wax toward the top of the unit by convection currents, as well as to the walls of the lens holder wells 34 and 36.

After substantially all of the wax has been melted, no futher heat input is required to supply the heat of fusion in melting the wax, and the temperature of the liquid wax will begin to rise above the melting temperature of the wax. When the molten wax reaches a predetermined temperature, the thermostatic switch in cavity 24 reaches its snap-off point. When that occurs, power is removed from the heating element and the unit begins to cool down. When the thermostatic switch is turned off, it remains off until it is manually reset.

It will be appreciated that although a particular embodiment of the invention has been shown and described, modifications may be made. It is intended in the following claims to cover all modifications which come within the true spirit and scope of the invention.

What is claimed is:

1. An electrically energized heating unit comprising: a bowl having an open top; an incubator supported on and covering the open top of the bowl, said incubator including at least one well extending into said bowl;

electrical heating means mounted in said bowl; wax contained in said bowl to be heated from a solid state to a molten state by said electrical heating means when the unit is energized so as to introduce heat into said well; at least a portion of said bowl being transparent and forming a window; and an indicator mounted in said bowl, displaced inwardly from said window, to be visible through said window when the wax in said bowl is in a molten state and to be invisible through said window when the wax in said bowl is in a solid state.

2. The electrically energized heating unit defined in claim 1, in which said bowl and said incubator are formed of plastic material, and are sealed to one another.

3. The electrically energized heating unit defined in claim 1, in which said indicator comprises an elongated strip, and said strip is mounted in said bowl in position to trap a predetermined quantity of the wax therein between the strip and the inner surface of the window.

* * * * *